(12) United States Patent
Mertens et al.

(10) Patent No.: US 7,407,912 B2
(45) Date of Patent: Aug. 5, 2008

(54) SUPERSUPERABSORBENT POLYMERS

(75) Inventors: Richard Mertens, Krefeld (DE); Olaf Höller, Greensboro, NC (US)

(73) Assignee: Stockhausen GmbH, Krefeld (DE)

( * ) Notice: Subject to any disclaimer, the term of this patent is extended or adjusted under 35 U.S.C. 154(b) by 689 days.

(21) Appl. No.: 10/721,821

(22) Filed: Nov. 25, 2003

(65) Prior Publication Data

US 2004/0157734 A1 Aug. 12, 2004

Related U.S. Application Data

(63) Continuation of application No. PCT/EP02/05799, filed on May 27, 2002.

(30) Foreign Application Priority Data

May 25, 2001 (DE) ................................ 101 25 599

(51) Int. Cl.
*B01J 20/00* (2006.01)
(52) U.S. Cl. ....................................................... 502/404
(58) Field of Classification Search .................. 502/404
See application file for complete search history.

(56) References Cited

U.S. PATENT DOCUMENTS

| | | |
|---|---|---|
| 2,639,239 A | 5/1953 | Elliott |
| 3,247,171 A | 4/1966 | Walker et al. |
| 3,589,364 A | 6/1971 | Dean et al. |
| 4,043,952 A | 8/1977 | Ganslaw et al. |
| 4,051,086 A | 9/1977 | Reid |
| RE31,323 E | 7/1983 | Marder et al. |
| 4,640,810 A | 2/1987 | Laursen et al. |
| 4,689,408 A | 8/1987 | Gelman et al. |
| RE32,649 E | 4/1988 | Brandt et al. |
| 4,952,550 A | 8/1990 | Wallach et al. |
| 4,959,341 A | 9/1990 | Wallach |
| 5,247,072 A | 9/1993 | Ning et al. |
| 5,247,964 A | 9/1993 | DeLange |
| 5,252,340 A | 10/1993 | Honeycutt |
| 5,470,964 A | 11/1995 | Qin |
| 5,532,350 A | 7/1996 | Cottrell et al. |
| 5,550,189 A | 8/1996 | Qin et al. |
| 5,669,894 A | 9/1997 | Goldman et al. |
| 5,807,116 A | 9/1998 | Kitatani et al. |
| 5,811,531 A | 9/1998 | Iguchi et al. |

FOREIGN PATENT DOCUMENTS

| | | |
|---|---|---|
| DE | 42 06 857 A1 | 3/1992 |
| DE | 44 18 319 A1 | 5/1994 |
| DE | 195 05 709 A1 | 2/1995 |
| DE | 196 54 745 A1 | 12/1996 |
| DE | 197 50 890 A1 | 11/1997 |
| DE | 198 07 501 C1 | 2/1998 |
| DE | 198 07 504 A1 | 2/1998 |
| DE | 199 09 653 A1 | 3/1999 |
| EP | 0 538 904 A2 | 4/1993 |
| EP | 0 538 904 B1 | 4/1993 |
| EP | 0 566 118 B1 | 10/1993 |
| EP | 0 614 914 B1 | 9/1994 |
| EP | 0 637 594 A2 | 2/1995 |
| EP | 0637 594 B1 | 2/1995 |
| EP | 0 855 405 A1 | 1/1998 |
| EP | 0 850 615 A1 | 7/1998 |
| EP | 1041109 A2 | 10/2000 |
| JP | 6 3037143 | 2/1988 |
| JP | 3 285919 | 12/1991 |
| JP | H06-154596 | 6/1994 |
| JP | 9 087956 | 3/1997 |
| JP | H09-504331 | 4/1997 |
| JP | 2000-345031 | 12/2000 |
| JP | 2001 114803 | 4/2001 |
| WO | WO 95/11925 | 5/1995 |
| WO | WO 99/49905 | 10/1999 |
| WO | PCT/EP02/05799 | 5/2002 |

OTHER PUBLICATIONS

Sibel Sungur, "Investigation on Drug Release Systems Using CMC Crosslinked with Ferric Ions", Art Cells, Blood Subs., And Immob. Biotech, (1999) 27 (3). 279-290.
Dictionary by Laborlawtalk, Internet website: http://dictionary.laborlawtalk.com/room_temperature, no date.
Prof. Dr. Jurgen Falbe and Prof. Dr. Manfred Regitz, Rompp Chemie Lexikon "Normalbedinguingen", article, copyright 1991, p. 3048, Georg Thieme Verlag Stuttgart, New York.

*Primary Examiner*—Edward M Johnson
(74) *Attorney, Agent, or Firm*—Smith Moore LLP

(57) ABSTRACT

The invention describes supersuperabsorbent polymers composed of surface-post crosslinked polycarboxypolysaccharides having excellent age-stable absorption properties, even under load, high attrition resistance and biodegradability and their use for absorbing water, aqueous or serous fluids and also blood. Also disclosed is a method of making which is impervious to changes in raw material quality and which provides consistent product quality.

54 Claims, No Drawings

SUPERSUPERABSORBENT POLYMERS

This application is a continuation of International Application No. PCT/EP02/05799, internationally filed May 27, 2002.

FIELD OF THE INVENTION

The invention relates to superabsorbent polymers based on surface modified polycarboxypolysaccharides. The superabsorbent polymers according to the present invention possess a high absorption capacity and rate, even under pressure, for water and aqueous solutions; have no gel-blocking tendency; and are mechanically robust. The superabsorption polymers are age stable, toxicologically safe and biodegradable. The present invention further relates to a simple process for preparing the supersuperabsorbent polymers and their use in hygiene articles, food-packaging materials, culturing vessels, for soil improvement and as cable sheathing.

BACKGROUND OF THE INVENTION

Most of the superabsorption polymers used today for their ability to take up large amounts of liquid (water, urine) in a short time are primarily lightly crosslinked synthetic polymers. They include, for example, polymers and copolymers based on acrylic acid or acrylamide, which are not based on renewable raw materials and which are insufficiently biodegradable, if at all.

Supersuperabsorbent polymers were initially developed with the focus solely on a very high swellability on contact with liquid, known as absorption or free swelling capacity (FSC), but it was subsequently determined that it is not just the amount of liquid which is absorbed that is important but also the gel strength. Absorption capacity on one hand and gel strength of a crosslinked polymer on the other hand, however, are contrary properties, as is already disclosed in U.S. Pat. No. 3,247,171 and U.S. Pat. No. Re 32,649. Superabsorbent polymers having a particularly high absorption capacity have little strength in the swollen gel state, so that a confining pressure, for example pressure due to the body of the wearer of a hygiene article, will cause the gel to deform and block further liquid distribution and absorption. According to U.S. Pat. No. Re 32,649, a balance should therefore be sought between the absorption capacity and the gel strength in order that, when such supersuperabsorbent polymers are used in a diaper structure, they ensure liquid absorption, liquid transport, diaper dryness and skin dryness.

A factor in this connection is not just that the freely swollen superabsorbent polymer be able to retain the absorbed liquid under a subsequent application of a pressure, but also that the superabsorbent polymer be capable of absorbing liquids even against a simultaneously (i.e. during the liquid absorption process) exerted pressure of the kind encountered in practice when an infant or adult sits or lies on a sanitary article or when shearing forces are developed, for example as a result of motion of the legs. This specific absorption characteristic is referred to in Edana method 442.1-99 as "Absorbency Against Pressure" or AAP for short. The AAP value reported for a supersuperabsorbent polymer is based on the pressure employed, for example, 21 g/cm² at 0.3 psi and 50 g/cm² at 0.7 psi. Also, the AAP may be based on the ratio chosen for the measurement of the supersuperabsorbent polymer weight to area, for example 0.032 g per cm², and also by the particle size distribution of a granular supersuperabsorbent polymer.

Patents EP 0 538 904 B1 and U.S. Pat. No. 5,247,072 disclose supersuperabsorbent polymers based on carboxyalkyl polysaccharides. To turn the carboxyalkyl polysaccharide into a supersuperabsorbent polymer, the carboxyalkyl polysaccharide is dissolved in water, isolated by drying or precipitation and subsequently thermally crosslinked via internal ester bridges formed by the reaction of the hydroxyl groups of the polysaccharide skeleton with the acidic carboxyl groups. Since this crosslinking reaction is very sensitive to small changes in the pH, temperature or reaction time, the superabsorbent polymers obtained have fluctuating absorption properties. The materials are notable for a high absorbency under load value which, however, deteriorates to a fraction of the initial value after ageing for a few weeks.

U.S. Pat. No. 5,550,189 discloses superabsorbent polymers based on carboxyalkyl polysaccharides that possess improved ageing stability owing to the addition of at least two-functional crosslinkers such as for example aluminum salts or citric acid. The superabsorbent polymers are prepared from a conjoint homogeneous aqueous solution of carboxyalkyl polysaccharide and crosslinkers, in which solution the components are present in low concentration and from which they are conjointly isolated and then thermally crosslinked. The synthesis of these superabsorbent polymers is very energy and time intensive, since the aqueous solutions are very weak. The improved ageing stability as it is reported in the majority of the illustrative embodiments does not meet actual service requirements.

EP 855 405 A1 addresses the poor ageing stability of the absorption capacity of swellable starch maleates and proposes by way of solution to this problem adding mercapto compounds to the double bond of the maleic acid substituent. The absorption performance of the product, especially under a confining pressure, is very poor.

U.S. Pat. No. 4,952,550 describes a method of making a superabsorbent polymer based on carboxymethylcellulose by treating the carboxymethylcellulose in water or organic solvents with polyvalent metal salts and a hydrophobicity agent. There is no thermal crosslinking step. According to the disclosure, the gel blocking of these superabsorbent polymers is reduced by the hydrophobicity agent.

The raw materials for preparing polysaccharide based supersuperabsorbent polymers are frequently soluble in water and have to be converted into a water-insoluble form for use as superabsorbent polymers for hygiene applications. Numerous existing processes involve a homogeneous crosslinking for the absorbent material in order that the water solubility of the absorbent may be reduced. This frequently has the disadvantage that such homogeneously crosslinked superabsorbent polymers no longer have the desired absorption capacity for liquids, since the swellability is excessively constrained by the crosslinking of the polymer chains.

Furthermore, homogeneous crosslinking compromises the biodegradability of the superabsorbent polymer, since the constrained swelling reduces the access for micro-organisms. In addition, the additionally introduced substituents inhibit enzymatic degradation [Mehltretter et al., Journal of the American Oil Chemists Society, 47 (1970) pages 522-524]. Attempts to ameliorate these disadvantageous properties have led to various surface treatment proposals.

U.S. Pat. No. 5,811,531 discloses the preparation of a superabsorbent polymer on the basis of polysaccharides, such as xanthan, which contain uronic acid groups by reacting the polysaccharides at the surface with at least two-functional organic crosslinkers. According to the disclosure, the products possess better free-swell absorbing ability against salt solutions than carboxyalkylated polysaccharides where the carboxyl groups are not attached directly to the saccharide units but via alkyl groups.

U.S. Pat. No. 5,470,964 discloses a process for preparing a superabsorbent polymer providing improved absorbency under load that is based on polysaccharides containing acid groups and is surface crosslinked by polyvalent metal ions. The disadvantages of this process are that the improved absorbency under load is achieved by the crosslinking of a relatively thick surface layer and that, according to the disclosure, this is only possible through prior incipient swelling of the polysaccharide with a large amount of solvent. The incipiently swollen state then allows sufficiently deep penetration of the polyvalent metal ions into the surface. To achieve this, the polysaccharide is introduced into an excess of the aqueous metal salt solution such that the weight ratio of polysaccharide to water is from 1:2 to 1:40. The thick crosslinked surface layer does provide good absorbency under load values, but the free swell capacity and also the retention capacity of the absorbent are disadvantageously reduced as a result. The process described has the further disadvantage that the polysaccharide portion added last to the crosslinker solution in the course of the manufacturing operation has less time to swell and encounters a lower crosslinker concentration, resulting in an inhomogeneous distribution of the crosslinker on the surface and hence fluctuations in the absorption properties.

U.S. Pat. No. 4,043,952 discloses the surface treatment of water-swellable anionic polyelectrolytes with polyvalent metal ions in a dispersing medium in which the polymer is insoluble to improve the dispersibility of the water-absorbent products.

The broad object underlying the invention is to overcome the disadvantages arising from the state of the art.

It is an object of the present invention to provide biodegradable supersuperabsorbent polymers based on renewable raw materials that are free of the defects described above. More particularly, the superabsorbent polymers shall have very long term storage stability with very substantial retention of the absorption properties. The absorbent particles shall also possess high mechanical robustness in order that the formation of fines in the course of processing operations such as, for example, screening or conveying may be avoided. Furthermore, with regard to the absorption performance, the superabsorbent polymers shall not gel-block and shall possess not only a high absorption and retention capacity but also a high absorbency against pressure with regard to water and aqueous solutions. Moreover, for an effective absorption and in-use performance, the superabsorbent polymers shall have an overwhelmingly insoluble character even in an excess of aqueous solution.

It is a further object of the present invention to provide a process for preparing such supersuperabsorbent polymers which is simple, economical and safe to carry out, which provides consistent product quality and which utilizes little solvent and ideally no organic solvent. Moreover, the processes shall not require toxicologically suspect substances to carry out.

A further object according to the invention consists in improving the biodegradability of hygiene articles such as sanitary napkins, wound dressings, incontinence articles and diapers.

SUMMARY OF THE INVENTION

These objects are achieved by a post crosslinked a superabsorbent polymer obtained by surface crosslinking at least one partly neutralized carboxyl-containing polysaccharide, characterized in that the polycarboxypolysaccharide is aqueous preswollen in uncrosslinked form and dried before the surface crosslinking.

The present invention is directed to a superabsorbent polymer comprising at least one partially neutralized, uncrosslinked, carboxyl-containing polysaccharide that is preswelled and subsequently dried, wherein the dried polycarboxypolysaccharide is surface-post crosslinked by means of a surface crosslinker.

In another embodiment, the present invention is directed to a superabsorbent polymer comprising at least one partially neutralized, uncrosslinked, carboxyl-containing polysaccharide that is preswelled and dried and surface-post crosslinking the dried polycarboxypolysaccharide by means of a surface crosslinker, wherein the polycarboxypolysaccharide includes one or more water-soluble additives from the group consisting of bases, salts and blowing agents or one or more anti-blocking additives from the group consisting of natural fiber materials, synthetic fiber materials, silica gels, synthetic silicas and water-insoluble mineral salts or any combination of at least two there from.

In another embodiment, the present invention is directed to a process for preparing a superabsorbent polymers comprising the steps of a) forming a hydrogel by mixing an uncrosslinked polycarboxypolysaccharide with water; b) the hydrogel is mechanically comminuted and dried; c) the dried hydrogel is comminuted and classified to form a polymer particles; and d) the superabsorbent polymer particles are coated with a solution of a crosslinker and subjected to a surface post crosslinking.

The present is further directed to absorbent hygiene articles that include the superabsorbent polymers of the present invention.

DESCRIPTION OF THE PREFERRED EMBODIMENTS

The present invention is directed to a superabsorbent polymer comprising at least one partially neutralized, uncrosslinked, carboxyl-containing polysaccharide that is preswelled and subsequently dried, wherein the dried polycarboxypolysaccharide is surface-post crosslinked by means of a surface crosslinker. One polysaccharide component used is a polycarboxypolysaccharide. Polycarboxypolysaccharides are either derived from polysaccharides which contain no carboxyl groups and are provided with carboxyl groups by subsequent modification or inherently already contain carboxyl groups and may optionally be provided with further carboxyl groups by subsequent modification. The first group of polysaccharides includes for example starch, amylose, amylopectin, cellulose and polygalactomannans such as guar and carob bean flour while the second group includes for example xanthan, alginates, and gum arabic.

The carboxyl groups, as mentioned, are either present inherently from the given molecular construction, for example due to uronic acid units in the polysaccharide molecule, or are introduced by subsequent modification with carboxyl-containing reagents or created by oxidation reactions. Of the polycarboxypolysaccharides where the carboxyl groups are introduced by subsequent modification, preference is given to the carboxyalkyl derivatives and especially to the carboxymethyl derivatives. Of the polycarboxypolysaccharides where the carboxyl groups are created by oxidation of the polysaccharide molecule, preference is given especially to oxidized starches and derivatives thereof.

The polycarboxypolysaccharides to be used according to the present invention are soluble or swellable in water and are used in non-crosslinked form. The polycarboxypoly-saccharides to be used according to the invention, as well as containing carboxyl groups, may be modified with further groups, especially with groups which improve the solubility in water, for example hydroxyalkyl and especially hydroxyethyl groups and also phosphate groups. Preferred polycarboxypolysaccharides are carboxymethylguar, carboxylated hydroxyethyl or hydroxypropylcellulose, carboxymethylcellulose and carboxymethylstarch, oxidized starch, carboxylated phosphatestarch, xanthan and mixtures thereof.

Polycarboxypolysaccharide derivatives having low and high degrees of carboxyl substitution are useful in the present invention. In a preferred embodiment, they have an average degree of carboxyl substitution in the range from about 0.3 to about 1.5 and preferably polycarboxypolysaccharide derivatives having a degree of substitution in the range from about 0.4 to about 1.2.

The preferred water-soluble polycarboxypolysaccharide derivatives have a high average molecular weight for the molecular weight distribution dictated by the natural polymer construction and hence they also have a high solution viscosity in dilute aqueous solution like for example carboxymethylcellulose prepared from cotton linters. In the case of carboxymethylcellulose, useful derivatives have a 1% aqueous solution viscosity of more than about 2000 mPas. Preference is given to using carboxymethylcellulose having a 1% aqueous solution viscosity of more than about 5000 mPas and more preferably of more than about 7000 mPas.

Their method of making polycarboxypolysaccharides is such that polycarboxypolysaccharides may include variable amounts of salt as a secondary constituent. Typical salt levels of carboxymethylcelluloses in food grades are of the order of 0.5% by weight, while typical salt levels of carboxymethylcelluloses in the case of technical grades range from about 2% by weight up to 25 to 50% by weight for products used as protective colloids. Although the superabsorbent polymers according to the invention are very tolerant to a salt burden, the polycarboxypolysaccharides to be used should not include more than about 15% by weight, preferably not more than about 5% by weight and more preferably not more than about 2% by weight of salt.

The superabsorbent polymers may be modified by addition of carboxyl-free polysaccharides. Preference is given to using swelling polysaccharides, for example polygalactomannans or hydroxyalkylcelluloses. The amounts of carboxyl-free polysaccharides used for modifying purposes are determined by the required performance profile and preference is given to using about 20% by weight, preferably about 10% by weight and more preferably about 5% by weight, based on the polycarboxypolysaccharide.

The carboxyl groups of the polycarboxypolysaccharides are at least about 80%, preferably at least about 90% and most preferably 100% neutralized. Useful neutralizing agents are alkali metal hydroxides such as sodium hydroxide, potassium hydroxide, sodium carbonate, potassium carbonate, sodium bicarbonate and potassium bicarbonate, ammonium hydroxide and amines.

The physical form of the polysaccharide derivatives used is immaterial to the properties of the superabsorbent polymers according to the invention. The polysaccharide derivatives may therefore be used for example in the form of powders, micro powders, granules, fibers, flakes, beads or compacts, in which case the use of pulverulent materials having a particle size in the range from 1 to 2000 µm is preferable for simplicity of metering and conveying.

The polycarboxypolysaccharide may be preswollen in an aqueous phase including, based on the polycarboxypolysaccharide, about 0.01 to about 20% by weight and preferably about 0.1 to about 10% by weight of water-soluble additives and about 0.01 to about 20% by weight and preferably about 0.1 to about 10% by weight of antiblocking additive to improve the processibility of the hydrogel being formed and to remain in the product at least to some extent after drying.

Water-soluble additives for the purposes of the invention are selected from the group consisting of bases, salts and blowing agents. Blowing agents are selected from inorganic or organic compounds which release a gas under the influence of catalysts or heat, for example, from azo and diazo compounds, carbonate salts, ammonium salts or urea.

Useful additives further include pH regulators such as for example alkali metal hydroxides, ammonia, basic salts such as, for example, alkali metal carbonates or alkali metal acetates. Useful additives further include neutral salts, for example, alkali metal or alkaline earth metal sulphates or chlorides, to regulate respectively the ionic strength of the solution and the salt content of the pulverulent superabsorbent resin.

The aqueous hydrogel may further have added to it water-miscible organic solvents, preferably water-miscible organic solvents which boil below about 100° C. These volatile organic solvents very substantially escape again from the hydrogel in the course of the subsequent drying step. These solvents are then completely volatilized in the course of the subsequent surface post crosslinking.

Antiblocking additives to further reduce the gel-blocking tendency of the pulverulent absorbent resin include, for example, native or synthetic fiber materials or other materials having a large surface area, for example, from the group consisting of silica gels, synthetic silicas and water-insoluble mineral salts.

The superabsorbent polymers according to the invention are surface post crosslinked. Following thermal drying, comminution and classification of the hydrogel, this crosslinking of the surface of the polycarboxypolysaccharide powder is affected with covalent and/or ionic crosslinkers which react with surface moieties, preferably carboxyl, carboxylate or hydroxyl groups, preferably by heating. Surface crosslinkers are used in an amount of about 0.01 to about 25% by weight and preferably about 0.1 to about 20% by weight based on the polysaccharide.

Covalent surface post crosslinking agents, which may be used alone or in combination with ionic crosslinkers, include crosslinkers which react with the functional groups on the polycarboxypolysaccharide to form covalent bonds. A preferred embodiment comprises using crosslinkers capable of reacting with the hydroxyl groups of the absorbent resin, for example, acid-functional substances.

Acid-functional substances include low molecular weight polycarboxylic acids and derivatives thereof, for example, malonic acid, maleic acid, maleic anhydride, tartaric acid and polymeric polycarboxylic acids, for example, based on (meth)acrylic acid and or maleic acid. Preference is given to the use of citric acid, butanetetracarboxylic acid and polyacrylic acid and particular preference is given to the use of citric acid. Citric acid is preferably used in an amount of about 0.2 to about 8% by weight and more preferably about 0.3 to about 6% by weight based on the polycarboxypolysaccharide. The polycarboxylic acids can also be used in partially neutralized form, for example, due to partial neutralization with alkali metal hydroxides or amine bases.

Ionic post crosslinking agents, which may be used alone or in combination with covalent post crosslinking agents, include salts of at least divalent metal cations, for example, alkaline earth metal ions such as $Mg^{2+}$, $Ca^{2+}$ and also $Al^{3+}$, $Ti^{4+}$, $Fe^{2+}/Fe^{3+}$, $Zn^{2+}$ or $Zr^{4+}$, of which $Al^{3+}$, $Ti^{4+}$ and $Zr^{4+}$ are preferred and $Al^{3+}$ is particularly preferred. Aluminum salts are preferably used in an amount of about 0.2 to about 1.0% by weight and preferably about 0.25 to about 0.85% by weight based on the polycarboxypolysaccharide.

The salts of the metal cations can be used not only alone but also mixed with each other. The metal cations in the form of their salts possess sufficient solubility in the solvent used, and particular preference is given to metal salts with weakly complexing anions such as, for example, chloride, nitrate, sulphate and acetate.

Post crosslinking agents further include post crosslinking agents capable of entering both covalent and ionic linkages, for example, di- and polyamines which can function not only as covalent crosslinkers, via amide groups, but also as ionic crosslinkers, via ammonium salt complexes. The covalent surface post crosslinking may optionally be increased by means of catalysts. Preferred catalysts are compounds which catalyze the esterification reaction between a carboxyl group and a hydroxyl group, for example, hypophosphites, acetylacetonates, mineral acids, for example, sulphuric acid, and Lewis acids. Preference is given to using sulphuric acid and hypophosphite. The weight ratio of surface post crosslinker to crosslinking catalyst is about 1:0001 to about 1:1 and preferably about 1:0.1 to about 2:1.

The solution whereby the surface post crosslinker is applied to the polycarboxypolysaccharide may optionally include one or more water-soluble additives to promote a homogeneous distribution of the crosslinker solution on the surface of the absorbent. In a preferred embodiment, the solution will include up to about 40% by weight of these additives. Such additives, as well as water-miscible organic solvents such as, for example, ethanol, propanol, 2-propanol, acetone, glycerol, tetrahydrofuran and dioxane, also include water-soluble organic solids such as, for example, polyalkylene glycols, polyvinyl alcohols and polyacrylic acids. Preference among organic solids is given to the use of polyethylene glycol. The preferred molecular weight range of the polyethylene glycol is not less than 1000 and especially not less than 1500.

In a preferred embodiment, the metal salts of divalent or higher cations function both as ionic surface crosslinkers and as additives for a homogeneous distribution of the crosslinker solution on the surface.

The particulate superabsorbent polymers according to the invention exhibit very good retention and absorption ability and a significantly improved absorbency for water and aqueous fluids against an external pressure in combination with an excellent ageing stability. The ageing stability shows itself in the fact that the absorbency against pressure ($AAP_{0.7}$) value after ageing for 200 days under standard conditions is at least 80% of the initial absorbency against pressure ($AAP_{0.7}$) value.

The absorption properties of the superabsorbent polymers according to the present invention show themselves in the fact that they can be made to have a retention of not less than about 15 g/g coupled with an absorbency against pressure ($AAP_{0.7}$) value of at least about 11 g/g and preferably of least about 15 g/g and preferably to have a retention of not less than about 20 g/g coupled with an absorbency against pressure ($AAP_{0.7}$) value of at least about 11 g/g and preferably of at least about 15 g/g and in another embodiment to have a retention of not less than about 25 g/g coupled with an absorbency against pressure ($AAP_{0.7}$) value of at least about 11 g/g and preferably of at least about 15 g/g.

The bulk density of the particulate absorbent resins according to the invention varies within the industrially customary range and is usually below about 1000 $g/dm^3$. In a preferred embodiment, the product has a bulk density of less than about 800 $g/dm^3$ and more preferably of less than about 650 $g/dm^3$.

Another feature is the attrition stability of the superabsorbent polymers according to the invention. Ball milling for 6 minutes (see "Mechanical Stability" test method) produces less than 5% of fines of below 150 μm. This high attrition stability provides substantially dustless processing of the superabsorbent polymers, for example, in diaper manufacturing equipment in which the superabsorbent polymers are exposed to mechanical stress in the course of conveyance.

Another feature is the biodegradability of the superabsorbent polymers under composting conditions in that degradation to water and carbon dioxide is at least 40% after 90 days and continues thereafter.

The surface post crosslinking according to the invention, in contradistinction to prior art products, is concentrated on a slight outer layer of extreme stability. This is determined by measuring the surface crosslinking index (SCI), which is the difference between the crosslinker concentrations in the attrited fines and the nonattrited absorbent. The higher the SCI index, the greater the amount of crosslinker removed with the fines of the superabsorbent polymer, i.e. the greater the concentration in which the crosslinker is present on the outer layer of the superabsorbent polymer. Superabsorbent polymers according to the invention preferably have an SCI index of greater than 40. When superabsorbent polymers have lower SCI values, the surface crosslinker has penetrated more deeply into the polymer particle, reducing the absorption properties.

The invention further provides a process for preparing the mechanically stable, surface post crosslinked superabsorbent polymer particles having significantly improved absorption properties coupled with consistent product quality by crosslinking the surface of a polycarboxypolysaccharide with a surface crosslinker, characterized in that a hydrogel is formed from an uncrosslinked polycarboxypolysaccharide with water, mechanically comminuted and dried. The dried hydrogel is comminuted and classified to form a superabsorbent polymer and in that the particles of the superabsorbent polymer are coated with a solution of a crosslinker and subsequently subjected to a surface post crosslinking step.

The process according to the invention affords particulate absorbent resins having very good retention and absorption ability and a significantly improved absorbency for water and aqueous fluids against an external pressure in combination with an excellent ageing stability and also a distinctly reduced solubility in aqueous solutions.

The process according to the invention completely yields age stable superabsorbent polymer, which retain their very good absorption properties even when stored for a prolonged period, yet are continuously biodegraded under composting conditions.

The first step of the process according to the present invention converts the polycarboxypolysaccharide derivative together with a solvent into a solid hydrogel, which optionally additionally includes further additives. The solvent used is particularly preferably water or a mixture of water with organic solvents such as, for example, ethanol, propanol, butanol, 2-propanol or acetone. In an embodiment, the polycarboxypoly-saccharide is presuspended in a mixture of water and organic solvent, if appropriate under elevated temperature, and converted into the hydrogel after separation from the suspension.

The hydrogel is preferably prepared by mechanically mixing the polycarboxypolysaccharide derivative with the solvent component in a continuous or batch operation. Suitable mixing means are, for example, batch kneaders such as trough kneaders, internal mixers or continuous kneaders such as single screw mixers or mixers having two or more screws.

To prepare the hydrogel, the level of polycarboxypolysaccharide in the mixture of polycarboxypolysaccharide and water can vary within wide limits. In one embodiment of the process, the level of polycarboxypolysaccharide in the mixture of polycarboxypolysaccharide and water is in the range from about 5 to about 65% by weight and more preferably from about 5 to about 55% by weight. To facilitate processing of the hydrogel, it can occasionally be necessary for the polycarboxypolysaccharide content not to exceed about 45% by weight. In another embodiment, the solvent is added to the dry polycarboxypolysaccharide raw material in a continuous operation, for example, in an extruder, and the process is operated in such a way that the solvent is present in deficiency.

It was found that the absorption properties of the superabsorbent polymers according to the present invention are minimally affected by the affectivity of the mixing or the homogeneity of the initially prepared hydrogel. The mixing of the individual components in a continuous mixing reactor with increasing throughput, for example, leads to less homogeneous hydrogels having increasing fractions of dry, nonswollen polymer fractions. It is believed that a subsequent swelling process takes place in the course of the further processing to pulverulent absorbent resins, so that the eventual absorption performance obtained is identical to that of completely homogeneously mixed gels.

The mixture of polycarboxypolysaccharide and water may according to the present invention additionally include up to about 30% by weight and preferably up to about 20% by weight of one or more organic solvents miscible with water and immiscible with the polycarboxypolysaccharide.

The ratio of solid components to solvent components can vary within wide limits and is chosen so that the resulting hydrogel has a firm and minimally tacky consistency. It is advantageous for the swollen gel, having been conveyed using a mincer or extruder, for example, and shaped using a breaker plate, to be in the form of firm extrudates which have no tendency to mutual adherence even in the course of prolonged storage. Gel consistency can be specifically adjusted via the weight fraction of organic water-soluble solvent in the hydrogel. The lower the concentration of the polycarboxypolysaccharide derivative in the hydrogel, the higher the weight fraction of the organic solvent has to be in order that the preferred gel consistency may be obtained. When, for example, the polycarboxypolysaccharide derivative used is a high molecular weight carboxymethylcellulose having a 1% aqueous solution viscosity of more than 4000 mPas and the solvent used is pure water, the preferred gel consistency is obtained at a polymer content of more than 15% by weight based on the swollen gel. Reducing the polymer fraction within the gel to less than 15% by weight gives a soft and tacky gel, which does not have the preferred consistency. However, on replacing 1-20% and preferably 5-15% by weight of the water solvent with an organic water-miscible solvent such as, for example, 2-propanol, which is a coagulant for carboxymethylcellulose and decreases the solubility of the polymer in the solvent mixture, even hydrogels having a polymer fraction of less than 15% by weight will have the preferred gel consistency. Reducing the polymer fraction to less than 10% by weight requires that the fraction of the organic solvent be correspondingly further increased to more than 15% by weight in order that the preferred gel consistency may be obtained.

The presence of an organic water-soluble solvent in the swollen gel not only has a positive effect on gel consistency, but also improves the absorption properties of the pulverulent superabsorbent significantly. This effect becomes clearly apparent even at low levels of less than 5% by weight based on the gel and shows itself in the absorbent resin particularly in a significantly higher absorption capacity for aqueous fluids against pressure.

The solvent or solvent mixture may further include 0.01-20% by weight and preferably 0.1-10% by weight, based on the solids content, of one or more water-soluble additives from the group consisting of bases, salts and blowing agents to improve the processibility of the swollen gel or the absorption properties of the absorbent resin and also to suppress any crosslinking reaction during the drying operation. Preferred additives are pH regulators such as, for example, alkali metal hydroxides, ammonia, basic salts such as, for example, alkali metal carbonates or acetates. Preferred additives further include neutral salts such as, for example, alkali metal or alkaline earth metal sulphates or chlorides for regulating the ionic strength of the solution and the salt content of the pulverulent absorbent resin. Additional additives used are preferably compounds which release gases under the action of catalysts or heat (blowing agents) and thus confer additional porosity on the hydrogel or absorbent resin whereby the absorption properties of the absorbent resin are additionally improved. Examples of blowing agents typically to be used are azo and diazo compounds, carbonate salts, ammonium salts and urea.

The hydrogel may further include 0.01-20% by weight preferably 0.1-10% by weight of one or more antiblocking additives to further reduce the gel-blocking characteristics of the pulverulent absorbent resin. Useful antiblocking additives include, for example, native or synthetic fiber materials or other materials having a large surface area, for example, from the group consisting of silica gels, synthetic silicas and substantially water-insoluble mineral salts.

In the next step of the process according to the invention, the hydrogel is comminuted and dried to low residual water content. The comminuting and drying step can immediately follow the preswelling step, but it is also possible to store the hydrogels for a prolonged period, for example, several weeks, prior to further processing without the properties of the resulting superabsorbent polymers according to the invention changing. Gel comminution particularly enlarges the ratio of gel surface area to gel volume, as a result of which the subsequent drying step requires substantially less energy input. The process of gel comminution is not subject to any limitation. In a particularly preferred embodiment, gel comminution is effected by pressing the gel through a breaker plate to form gel extrudates which may if appropriate be divided into shorter gel extrudates by a cutting tool.

As regards drying the hydrogel particles, various processes are known. Possible processes include, for example, vaporizative drying, evaporative drying, irradiative drying (example: infrared drying), high frequency drying (example: microwave drying), vacuum drying, freeze-drying or spray drying. The drying can accordingly be carried out, for example, according to the thin film drying process, for example, using a biaxial can dryer; according to the plate drying process, whereby the hydrogel polymer particles are loaded on plates in multiple layers into a drying chamber in which hot air circulates; by the rotating drum process using can dryers; or by the conveyor belt process, herein below also referred to as belt drying. Belt drying, where foraminous trays of a circle conveyor are loaded in a tunnel with the material to be dried and the material is dried by blowing hot air through the tray holes during the passage through the tunnel, constitutes the most economical drying process for water-swellable hydrophilic hydrogels and therefore is preferred.

The moisture content of the polymer powder formed by drying the hydrogel is advantageously not above 30% by weight, preferably not above 15% by weight and more preferably not above 10% by weight.

The addition polymer gel is dried at temperatures above about 70° C., preferably above about 120° C. and more preferably above about 130°. The parameters such as the polymer content of the hydrogel, the pH of the solvent system, the method of mixing, the drying temperature and the drying time are interdependent and are preferably attuned to each other in such a way that no internal crosslinking of the hydrogel takes place during the drying step. If, for example, a solvent having a pH below 7 is used to make the hydrogel, some of the carboxylate groups present in the polysaccharide derivative are converted into the free acid form and are accordingly able, towards the end of the drying step in particular, to act as internal crosslinkers through an esterification with the hydroxyl groups. To control this fundamentally undesirable internal crosslinking, the drying in these cases preferably takes place at temperatures in the range of 70-100° C. The pH is usually set to 6 or higher. In a preferred embodiment of the invention, the hydrogel is prepared using a solvent having a pH of 7 or more and drying at temperatures of not less than 120° C., preferably from 130 to 160° C.

If the hydrogel is prepared in a continuous mixer, for example, an extruder, the precursor products obtained at a pH of not less than 7 and which as yet have not been surface post crosslinked may have high retention values of not less than 40 g/g, which turn out to be stable to heat treatment at 120° C. for 60 minutes and which differ only minimally from products prepared at a higher pH. If, by contrast, the hydrogels are prepared in a batch operation, the stability to heat treatment increases with increasing hydrogel pH. A preferred pH for hydrogel formation in a batch operation is pH 10 or higher.

It was found that, the particularly preferred drying temperatures of above about 130° C. provide superabsorbent polymers having a significantly higher absorption and retention ability coupled with comparable absorbency against an external pressure.

For the subsequent grinding of the dried hydrogel particles it is advantageous to cool the dried material to temperatures of 70° C. or less, preferably 60° C. or less and more preferably 50° C. or less in the last section of the preferred belt drying stage. The cooled dried hydrogel particles are initially prebroken, for example, by means of a knuckle-type crusher. The thus precomminuted hydrogel particles are then ground, preferably by means of a roll mill in order that the production of fines may be minimized. In a particularly preferred embodiment, the grinding is carried out in two stages, first via a coarse roll mill and then via a fine roll mill, and the latter may in turn be carried out in one or two stages.

Screening is carried out subsequently to set the particle size distribution, which is generally between 10 and 3000 μm, preferably between 100 and 2000 μm and more preferably between 150 and 850 μm. Oversize particles may be resubmitted to grinding, while undersize particles may be recycled back into the forming operation.

The surface coating of the superabsorbent polymer with 0.01 to 25% by weight and preferably 0.1 to 20% by weight based on the addition polymer of a post crosslinker which is supplied in the form of a 0.01 to 80% by weight and preferably 0.1 to 60% by weight solution is carried out in suitable mixing assemblies. These are, for example, Paterson-Kelly mixers, DRAIS turbulence mixers, Lödige mixers, Ruberg mixers, screw mixers, pan mixers, fluidized bed mixers or Schugi mixers. The application of the crosslinker solution by spraying may be followed by a heat treatment step, preferably in a downstream dryer, at a temperature between 40 and 250° C., preferably 60-200° C. and more preferably 80-160° C. for a period of 5 minutes to 6 hours, preferably 10 minutes to 2 hours and more preferably 10 minutes to 1 hour to remove solvent fractions. The optimum duration of the subsequent heating operation can easily be determined for the individual crosslinker types in a few experiments. One limit for the duration is reached when the performance profile desired for the superabsorbent is destroyed again as a consequence of heat damage. The thermal treatment can be carried out in customary dryers or ovens; examples of suitable dryers and ovens are rotary tube ovens, fluidized bed dryers, pan dryers, paddle dryers and infrared dryers.

It has been determined to be advantageous in some instances for the aqueous solution of the surface post crosslinker to be adjusted to a temperature of 15° C.-100° C. and preferably to 20° C.-60° C. before use.

The time for covalent surface post crosslinking can be decreased by the use of catalysts. Preferred catalysts are compounds which catalyze the esterification reaction between a carboxyl group and a hydroxyl group, for example hypophosphites, acetylacetonates, mineral acids, for example, sulphuric acid, and Lewis acids. Preference is given to using sulphuric acid and hypophosphite. The weight ratio of surface post crosslinker to crosslinking catalyst is 1:0.001-1:1 and preferably 1:0.1-2:1. In a preferred embodiment, the crosslinking catalysts are mixed into the solution of the surface post crosslinker.

The post crosslinking solution may optionally include up to 70% by weight of one or more additives. Additives are in particular water-soluble compounds which promote a homogeneous distribution of the crosslinker solution on the surface of the absorbent by slowing the penetration of the solvent into the interior of the superabsorbent particle and also reduce the solubility of the particle surface and hence the tendency of the moist superabsorbent particles to adhere to each other. Preferred additives, as well as water-miscible organic solvents such as, for example, ethanol, propanol, 2-propanol, acetone, glycerol, tetrahydrofuran and dioxane, also include water-soluble hydrophilic organic solids, especially polymers such as, for example, polyalkylene glycols, polyvinyl alcohols and preferably polyethylene glycols.

In a preferred embodiment, the metal salts of divalent or higher cations function both as ionic surface crosslinkers and as additives for a homogeneous distribution of the crosslinker solution on the surface.

The superabsorbent polymers according to the invention are notable for absorption and retention ability for water, aqueous solutions and body fluids. At the same time, due to the controlled crosslinking of surface, the superabsorbent polymers possess an improved absorbency for aqueous solutions against an external pressure. In addition, the superabsorbent polymers according to the invention, which are based on polycarboxypolysaccharide derivatives, are stable in storage, free of residual monomer fractions, only minimally soluble in aqueous fluids and biodegradable.

The superabsorbent polymers according to the invention are very useful as superabsorbent polymers in hygiene articles such as, for example, infant and adult diapers, wound contact materials, sanitary napkins, tampons and the like. The superabsorbent polymers are especially suitable for use in hygiene articles which are to be composted after use, since the polymers have proved biodegradable in composting tests in accordance with ASTM method D 5338-92 of 15.12.1992; in accordance with the CEN draft "Evaluation of the Ultimate Aerobic Biodegradability and Disintegration of Packaging Materials under Controlled Composting Conditions" of 6.5.1994; and in accordance with DIN 54900 Part 2 Method 3 of January 1997.

Absorbent hygiene products typically possess a general construction composed of a body facing liquid-pervious topsheet (1), a liquid-absorbent layer (2) and a substantially liquid-impervious body remote outer layer (3). Further structures may optionally find application in the absorbent core to rapidly acquire and distribute body fluid (4). These structures are frequently but not necessarily used between the body facing liquid-pervious topsheet (1) and the liquid-absorbent layer (2).

The liquid-pervious topsheet (1) is typically composed of a fibrous nonwoven or some other porous structure. Useful materials for this topsheet (1) include, for example, synthetic polymers such as polyvinyl chloride, polyvinyl fluoride, polytetrafluoroethylene (PTFE), polyvinyl alcohols and derivatives, polyacrylates, polyamides, polyesters, polyurethanes, polystyrene, polysiloxanes or polyolefins (e.g. polyethylene (PE) or polypropylene (PP)) and also natural fiber materials and also any desired combinations of the aforementioned materials in the form of hybrid materials, composite materials or copolymers.

The liquid-pervious topsheet (1) has a hydrophilic character. It may also constitute a combination of hydrophilic and hydrophobic constituents. Preference is generally given to a hydrophilic finish for the liquid-pervious topsheet (1) in order that rapid seepage of body fluid into the liquid-absorbent layer (2) may be ensured, but partially hydrophobicized topsheets (1) are used as well.

The liquid-absorbent layer (2) includes the superabsorbent powders or granules according to the invention and further components composed, for example, of fibrous materials, foam materials, film-forming materials or porous materials and also combinations of two or more thereof. Each of these materials can be of natural or synthetic origin and may have been prepared by chemical or physical modification of natural materials. The materials can be hydrophilic or hydrophobic, in which case hydrophilic materials are preferred. This applies especially to those compositions which are to efficiently acquire secreted body fluids and transport them in the direction of regions of the absorbent core which are more remote from the point of ingress of the body fluid.

Useful hydrophilic fiber materials include, for example, cellulosic fibers, modified cellulosic fibers (for example stiffened cellulosic fibers), polyester fibers (for example, Dacron), hydrophilic nylon or else hydrophilicized hydrophobic fibers, for example, surfactant-hydrophilicized polyolefins (PE, PP), polyesters, polyacrylates, polyamides, polystyrene, polyurethanes and others.

Preference is given to using cellulosic fibers and modified cellulosic fibers.

Combinations of cellulosic fibers and/or modified cellulosic fibers with synthetic fibers such as, for example, PE/PP bicomponent fibers as used, for example, to thermobond airlaid materials or other materials are likewise customary. The fiber materials can be present in various use forms, for example, as loose cellulosic fibers deposited or laid down from an air stream or from an aqueous phase, as a nonwoven or as a tissue. Combinations of various use forms are possible.

The superabsorbent polymers according to the invention may optionally include further pulverulent substances, for example, odor-binding substances such as cyclodextrins, zeolites, inorganic or organic salts and similar materials.

The liquid-absorbent layer (2) may be mechanically stabilized using thermoplastic fibers (for example, bicomponent fibers composed of polyolefins), polyolefin granules, latex dispersions or hot melt adhesives. Optionally, one or more layers of tissue are used for stabilization.

The liquid-absorbent layer (2) can be a single layer or be composed of a plurality of layers. Preference is given to the use of structures constructed of hydrophilic fibers, preferably cellulosic fibers, optionally a structure to rapidly acquire and distribute body fluid (4) such as, for example, chemically stiffened (modified) cellulosic fibers or high loft webs composed of hydrophilic or hydrophilicized fibers and also superabsorbent polymers.

The superabsorbent polymer according to the invention can be homogeneously distributed in the cellulosic fibers or stiffened cellulosic fibers, it can form a layer between the cellulosic fibers or stiffened cellulosic fibers, or the concentration of the superabsorbent polymer can have a gradient within the cellulosic fibers or stiffened cellulosic fibers. The ratio of the total amount of superabsorbent polymer and of the total amount of cellulosic fibers or stiffened cellulosic fibers in the absorbent core can vary between 0:100 and 70:30%, although one embodiment provides local concentrations of up to 100% of superabsorbent, for example, in the case of gradiented or layered incorporation. Such structures feature regions of high concentrations of superabsorbent polymer, the fraction of superabsorbent being between 60 and 100% and most preferably between 90% and 100% in certain regions.

It is optionally to use at the same time two or more different superabsorbent polymers which differ, for example, in the absorption rate, the permeability, the storage capacity, the absorbency against pressure, the particle size distribution or else the chemical composition. The various superabsorbent polymers can be introduced into the absorbent core after blending with each other or else can be placed in the absorbent pad with local differentiation. Such a differentiated placing can be effected in the direction of the thickness of the absorbent core or in the direction of the length or in the direction of the width of the absorbent pad.

The liquid-absorbent layer (2) includes one or more of the above-described cellulosic fiber or stiffened cellulosic fiber layers containing superabsorbent polymers. A preferred embodiment utilizes structures composed of combinations of layers featuring homogeneous superabsorbent incorporation and additionally layered incorporation.

These aforementioned structures are optionally also supplemented by further layers of pure cellulosic fibers or stiffened cellulosic fibers on the body facing side and/or else the body remote side. The above-described structures can also repeat a number of times, in which case there may be a superposition of two or more identical layers or else a superposition of two or more different structures. The differences are in turn purely structural or else in the type of material used, for example, the use of superabsorbent polymers differing in terms of properties or else the use of different pulp varieties. Optionally, the entire absorbent pad or else individual layers of the liquid-absorbent layer (2) are separated from other components by layers of tissue or are in direct contact with other layers or components.

By way of example, the structure for rapid acquisition and distribution of body fluid (4) and the liquid-absorbent layer (2) can be separated from each other by tissue or else be in direct contact with each other. If there is no separate structure to rapidly acquire and distribute body fluid (4) between the liquid-absorbent layer (2) and the body facing liquid-pervious topsheet (1), but the fluid distribution effect is to be achieved, for example, by the use of a specific body facing liquid-pervious topsheet (1), the liquid-absorbent layer (2) can optionally likewise be separated from the body facing liquid-pervious topsheet (1) by a tissue.

Instead of tissue it is optionally also possible for a nonwoven to be incorporated into the liquid-absorbent layer (2). Either component brings about the desired secondary effect of stabilizing and strengthening the absorbent core in the moist state.

Fibrous layers which contain superabsorbent and distribute and store liquid can be generated using a multiplicity of production processes. As well as the established conventional operations as generally subsumed by those skilled in the art under drum forming using forming wheels, forming pockets and product forms and correspondingly adapted metering means for the raw materials, customary methods for producing the abovementioned liquid stores include modern established processes such as airlaid, with all forms of metering, fiber letdown and consolidation such as hydrogen bonding, thermal bonding, latex bonding and hybrid bonding, wetlaid, carding, meltblown and spunblown operations and similar operations for producing superabsorbent-containing nonwovens singly and combined with and among each other.

Further processes include the production of laminates in the widest sense and also of extruded and coextruded, wet-consolidated and dry-consolidated and also subsequently consolidated structures. A combination of these processes with and among each other is likewise possible.

A structure for rapid acquisition and distribution of body fluid (4) is composed, for example, of chemically stiffened (modified) cellulosic fibers or high loft webs composed of hydrophilic or hydrophilicized fibers or a combination of both.

Chemically stiffened, modified cellulosic fibers can be produced, for example, from cellulosic fibers which are reacted by means of crosslinkers such as, for example, $C_2$-$C_8$ dialdehydes, $C_2$-$C_8$ monoaldehydes having an additional acid function or $C_2$-$C_9$ polycarboxylic acids in a chemical reaction. Specific examples are glutaraldehyde, glyoxal, glyoxalic acid or citric acid. Also known are cationically modified starch or polyamide-epichlorohydrin resins (i.e., KYMENE® 557H, Hercules Inc., Wilmington, Del.). The crosslinking provides and stabilizes a twisted, curled structure which has an advantageous effect on the rate of fluid acquisition.

The absorbent hygiene products can differ widely in basis weight and thickness and hence density. Typically the densities of the regions of the absorbent cores are between 0.08 and 0.25 g/cm$^3$. The basis weights are between 10 and 1000 g/m$^2$, although it is preferable to provide basis weights between 100 and 600 g/m$^2$. The density varies in general along the length of the absorbent core. This is a consequence of a controlled metering of the cellulosic fiber or stiffened cellulosic fiber quantity or the quantity of the superabsorbent polymer, since these components are in preferred embodiments preferentially incorporated in the front region of the disposable absorbent article.

This controlled increase in the absorbent material in certain regions of the absorbent core can also be achieved, for example, by producing an appropriately sized airlaid or wetlaid sheet material composed of hydrophilic cellulosic fibers, optionally of stiffened cellulosic fibers, optionally of synthetic fibers (e.g. polyolefins) and also of superabsorbent polymers and subsequent back rolling or superposition.

The polymers according to the invention are also used in absorbent articles which are suitable for a wide variety of uses, for example, by mixing with paper or fluff or synthetic fibers or by distributing the superabsorbent polymers between substrates of paper, fluff or nonwoven textiles or by processing into base materials to form a continuous length. The polymers according to the invention are further used wherever aqueous fluids have to be absorbed, for example, in cable sheaths, in food packaging, in the agricultural sector for plant cultivation and as water storage medium and also as a carrier for an active component to be released to the environment in a controlled manner.

The products according to the invention which have a good combination of very high absorption and retention values, excellent absorbency against pressure and biodegradability can be prepared without the use of toxicologically compromised substances. According to the invention, the polymers can be produced on a large industrial scale according to existing processes in a continuous or batch wise manner and with consistent product quality.

The invention is further concerned with structures for absorbing body fluids, comprising a polymer according to the invention. These aforementioned structures are preferably absorbent bodies. In another embodiment of the construction it is a sanitary napkin, a diaper or an incontinence product, wherein diapers are particularly preferred.

Test Methods

Retention (TB)

The retention values were determined by performing a tea bag test. The test solution used was a 0.9% strength NaCl solution. 0.20 g of the test substance (screened off between 150 and 850 μm) were sealed into a tea bag and immersed in the test solution for 30 minutes. The tea bag was subsequently spun in a centrifuge, for example, a commercially available laundry spin dryer, at 1400 rpm for 3 minutes. The amount of liquid absorbed was determined gravimetrically after subtraction of the blank value (weight of an empty tea bag after spinning) and converted to 1 g of test substance. The retention value corresponds to the amount of liquid absorbed in grams per gram of test substance.

Absorbency Against a Pressure of 0.3 or 0.7 psi (AAP)

The ability to absorb a liquid against an external pressure (absorbency against pressure, AAP) was determined as per Edana method No. 442.1-99. 0.90 g of the test substance (screened off between 150 and 850 μm) was weighed into a test cylinder having an internal diameter of 60.0 mm and a 400 mesh screen base (concentration: 0.032 g/cm$^2$) and uniformly distributed therein. Onto the test substance is placed a cylindrical weight (21 g/cm$^2$=0.3 psi or 50 g/cm$^2$=0.7 psi) having an outer diameter of 59.2 mm. Filter plates covered with a filter paper are placed in a plastic dish. The plastic dish is filled with 0.9% strength NaCl solution until the surface of the liquid is flush with the upper edge of the filter plates. The prepared measuring units are then placed on the filter plates. After a swell time of 60 minutes the measuring units are taken out and the weight is removed. The amount of liquid absorbed is determined gravimetrically and converted to 1 gram of test substance.

Extractables (EA)

Extractable fractions in the biodegradable superabsorbent resins were determined by GPC analysis under the following test conditions.

Column material: HEMA BIO 40, column length: 300 mm, column diameter: 8 mm eluent: 0.9% NaCl solution, flow rate: 1.0 ml/minute, temperature: room temperature, injection volume: 50 μl, running time 15 minutes, calibrating substance: low viscosity carboxymethylcellulose (Finnfix® 4000 G).

0.50 g of the test substance is admixed with 100 ml of 0.9% strength NaCl solution and stirred for 16 hours. After filtration through a glass filter crucible (pore size 1) the filtrate was diluted with the eluent in a ratio of 1:10. This dilution was injected and the area value of the polymer peak determined. The soluble fraction of the test substance was calculated by means of a calibration curve prepared with the low viscosity carboxymethylcellulose under identical conditions.

Fluff-absorbent Combination Test (FACT)

2.0 g of cellulose fluff were weighed out on an analytical balance and formed into three fluff layers. 0.22 to 2 g (=10 to 50% by weight) of superabsorbent polymer was uniformly sprinkled between the fluff layers so as to create a fluff/SAP/fluff/SAP/fluff sandwich. The fluff-superabsorbent pad was placed in a test apparatus having a screen base and weighted with a metal ring to stop the absorbent resin escaping from the test apparatus as it swells. The test specimen was loaded with a weight (21 g/cm$^2$ or 50 g/cm$^2$ corresponding to 0.3 psi and 0.7 psi respectively). The test specimen was then allowed to swell in 0.9% strength NaCl solution by capillary action while the absorption was recorded by electronic data processing. The test was deemed to have ended when less than 1 g of test liquid was absorbed in the course of 10 minutes. For every measurement, the amount of liquid absorbed was plotted against time in an absorption curve from which the following parameters were determined:
a) maximally attained end value in grams: $Abs_{max}$
b) time [min] at which the end value was attained: $t_{max}$
c) time [min] at which x% of the final value was attained: $t_{x\%}$ Airlaid Tests An airlaid machine was used to fabricate composite materials composed of one layer of tissue, a subsequent layer of a cellulose fluff-absorbent powder mix and a further layer of tissue. Round specimens 6 cm in diameter were die cut from the composite and used for the subsequent tests.

Composite Retention

A tea bag test was carried out to determine the retention values of the composite. The test solution used was a 0.9% strength NaCl solution. A die cut composite specimen was weighed, sealed into a tea bag and immersed in the test solution for 30 minutes. The tea bag was subsequently spun in a centrifuge, for example, a commercially available laundry spin dryer, at 1400 rpm for 3 minutes. The amount of liquid absorbed was determined gravimetrically after subtraction of the blank value (weight of empty tea bag after spinning) and converted to 1 m$^2$ of composite. The retention value corresponds to the amount of liquid absorbed in grams per square meter of airlaid composite.

Absorbency of a composite against a pressure of 20 or 50 g/cm$^2$ (LAUL20/LAUL50). A die cut composite specimen was weighed into a test cylinder having an internal diameter of 60.0 mm and a 400-mesh screen base. A cylindrical weight (20 g/cm$^2$ or 50 g/cm$^2$) having an external diameter of 59.2 mm is placed onto the test substance. Filter plates are placed into a plastic dish and covered with a filter paper. The plastic dish is filled with 0.9% strength NaCl solution until the surface of the liquid is level with the upper edge of the filter plates. The prepared measuring units are then placed on the filter plates. After a swell time of 60 minutes the measuring units are taken out and the weight is removed. The amount of liquid absorbed is determined gravimetrically and converted to 1 square meter of airlaid composite.

Mechanical Stability 127 g of grinding media (cylindrical pieces of porcelain, U.S. Stoneware ½" O.D. * ½") and 10 g of a pulverulent superabsorbent resin having a particle size of 150 to 850 μm were weighed into a ball mill pot. The ball mill pot was sealed and rotated at 95 rpm on a roll mill for 6 minutes. The mechanically stressed superabsorbent was taken from the pot and analyzed with regard to particle size distribution.

Surface Crosslinking Index (SCI)

127 g of grinding media (cylindrical pieces of porcelain, U.S. Stoneware ½" O.D. * ½") and 10 g of a surface-crosslinked superabsorbent resin having a particle size of 150 to 850 μm were weighed into a ball mill pot. The ball mill pot was sealed and rotated at 95 rpm on a roll mill for 30 minutes. The mechanically stressed superabsorbent was taken from the pot and the particles having a particle size <150 μm were screened out. The screened-off fines were digested with $HNO_3$ and $H_2O_2$ using a microwave and subsequently hydrolyzed with water. The aluminum content was then determined photometrically via the yellowish red Alizarin S-aluminum complex. The SCI is calculated from the amount of $Al^{3+}$ added in the course of the surficial crosslinking, based on the superabsorbent resin (=$C_{SAP}$), and the $Al^{3+}$ concentration of the fine particles found after mechanical exposure (=$C_F$) in accordance with the equation SCI=$(C_F-C_{SAP})*100$, where $C_F$ and $C_{SAP}$ are inserted in % $Al^{3+}$.

EXAMPLES

All superabsorbent polymers according to the invention were, unless otherwise stated, ground prior to surface coating and screened off to a particle size of 150 to 850 μm. The moisture content of all pulverulent absorbent resins was less than 10% by weight.

Example 1

Preparation of Precursor Hydrogel

In a make-up vessel, 100 g of carboxymethylcellulose (CMC) were suspended in a mixture of 244 g of 2-propanol and 156 g of DM water and refluxed for 1 hour. After the suspension had been cooled to room temperature, the carboxymethylcellulose was filtered off. A second make-up vessel was charged with 900 g of water which was adjusted to pH 9 with NaOH. The filtered-off carboxymethylcellulose was introduced into the second make-up vessel with vigorous stirring to form a firm hydrogel. After a swell time of 30 minutes, the swollen hydrogel was fed into a meat mincer equipped with a mincer plate and comminuted. The comminuted hydrogel was dried at 80° C. in a circulating air cabinet for 12 hours. The dried hydrogel was coarsely comminuted and ground using a Retsch mill. After the particle size fraction of 150 to 850 μm had been screened off, the retention value of the uncrosslinked precursor was determined. Table I includes various precursor variations and the retention values thus determined for various commercially available carboxymethylcelluloses (CMCs):

TABLE 1

Precursor Variations of Example 1

| No CMC | Viscosity [mPas] | D.S.[a] | Precursor retention [g/g] |
|---|---|---|---|
| 1.1 Finnfix ® 50,000[b] | 8,200 (1%) | 0.78 | 46.5 |
| 1.2 Cekol ® 50,000[b] | 8,400 (1%) | 0.72 | 47.0 |
| 1.3 Cekol ® 100,000[b] | 10,000 (1%) | 0.76 | 32.2 |

TABLE 1-continued

Precursor Variations of Example 1

| No CMC | Viscosity [mPas] | D.S.[a] | Precursor retention [g/g] |
|---|---|---|---|
| 1.4 Tylose ® CB 30,000[c] | >24,000 (2%) | >0.85 | 45.3 |
| 1.5 Blanose ® 7HOF[d] | 2140 (1%) | 0.85 | 36.8 |
| 1.6 Walocel ® VP-C-2204[e] | >7500 (1%) | 0.65-0.95 | 44.7 |

[a]Degree of substitution as per manufacturer data,
[b]Noviant,
[c]Clariant,
[d]Aqualon,
[e]Wolff-Walsrode

Example 2

A crosslinker solution was prepared from 1.29 g of citric acid monohydrate, 61 g of 2-propanol and 39 g of DM water. 10 g of each of the pulverulent precursors prepared according to Example 1) were each coated with 4 g of this crosslinker solution (corresponding to a citric acid concentration of 0.47% based on CMC) and dried at 80° C. for 2 hours. Surface crosslinking was completed by a subsequent annealing step for the stated period at 120° C. The annealing time was chosen so as to ensure a balanced ratio of retention to absorbency against pressure. The superabsorbent polymers thus prepared had the following characteristic data as shown in Table 2:

TABLE 2

Example 2 Variations

| No | Precursor of inv. ex. | Annealing [min] | TB [g/g] | $AAP_{0.3}$ [g/g] | $AAP_{0.7}$ [g/g] |
|---|---|---|---|---|---|
| 2.1 | 1.1 | 30 | 24.0 | 21.6 | 14.4 |
| 2.2 | 1.2 | 50 | 21.0 | 20.5 | 16.1 |
| 2.3 | 1.3 | 30 | 19.4 | 20.9 | 16.8 |
| 2.4 | 1.4 | 30 | 20.4 | 21.8 | 17.2 |

Example 3

Various crosslinker solutions were prepared by adding acetone to an aqueous solution of aluminum sulphate 18-hydrate in DM water:
A: 13 g of $Al_2(SO_4)_3$*18 $H_2O$/100 g of DM water and 36.7 g of acetone
B: 18 g of $Al_2(SO_4)_3$*18 $H_2O$/100 g of DM water and 36.1 g of acetone 10 g of each of the precursors of Example 1 were each coated with 4 g of each crosslinker solution thus prepared by initially charging the pulverulent precursor and adding the crosslinker solution drop wise with stirring. The coated product was dried at 80° C. for 2 hours and the dried products were measured for retention and APP:

TABLE 3

Example 3 Variations

| No | Precursor of inv. ex. | Crosslinker solution | % $Al^{3+}$/CMC | TB [g/g] | $AAP_{0.3}$ [g/g] | $AAP_{0.7}$ [g/g] |
|---|---|---|---|---|---|---|
| 3.1 | 1.1 | B | 0.38 | 24.1 | 18.9 | 13.6 |
| 3.2 | 1.2 | A | 0.28 | 22.6 | 20.5 | 16.1 |
| 3.3 | 1.3 | B | 0.38 | 18.3 | 17.9 | 14.8 |
| 3.4 | 1.6 | B | 0.38 | 22.8 | 18.6 | 14.1 |

Example 4

Carboxymethylcellulose (Finnfix® 50,000) was preswollen and dried, both steps being carried out as described in Example 1). 50 g of the uncrosslinked precursor thus prepared were weighed into a plastic cup and stirred using a household mixer. 3 g of a solution consisting of 3.33 g of citric acid monohydrate and 17.5 g of polyethylene glycol (1 500 g/mol) in 29.2 g of DM water were poured onto the pulverulent precursor in the course of 10 seconds, followed by stirring for a further 100 seconds. The coated absorbent was cured at 120° C. for 45 minutes and showed the following characteristic data:

Example No. 4.1:    TB = 22.2 g/g    $AAP_{0.7}$ = 13.3 g/g

Example 5

Example 4) was repeated, except that the 3.0 g of coating solution used was composed of 5.5 g of polyacrylic acid ($M_w$ 1 500 g/mol) and 0.39 g of sodium hydroxide in 10.0 g of DM water:

Example No. 5.1:    TB = 23.2 g/g    $AAP_{0.7}$ = 13.0 g/g

Example 6

Carboxymethylcellulose (Finnfix® 50,000) was mixed with the stated amounts of guar bean flour. The powder mixture was preswollen and dried, both steps being carried out as described in Example 1). 10 g of each of the dried pulverulent precursors are coated with 4 g of a solution of 0.85 g of citric acid monohydrate in 99.15 g of 2-propanol and dried at 80° C. for 2 hours. The crosslinking reaction was then completed at 120° C. for 30 minutes.

TABLE 4

Example 4 Variations

| No | % by weight of guar bean flour | TB [g/g] | $AAP_{0.3}$ [g/g] | $AAP_{0.7}$ [g/g] |
|---|---|---|---|---|
| 6.1 | 5 | 22.4 | 19.1 | 12.7 |
| 6.2 | 10 | 22.5 | 17.5 | 13.1 |
| 6.3 | 20 | 16.2 | 16.5 | 12.8 |

Example 7

In a make-up vessel, 600 g of carboxymethylcellulose (Cekol® 50,000, degree of neutralization 98.6%) were suspended in a mixture of 1,460 g of 2-propanol and 940 g of DM water and refluxed for 1 hour. The suspension was cooled down to room temperature and filtered. A second make-up vessel was charged with 5000 g of DM water which were then adjusted to pH 9 with 2.5 g of 10% strength aqueous sodium hydroxide solution. The filter cake was introduced into the second make-up vessel with strong stirring and the hydrogel formed was comminuted after 1 hour in a meat mincer equipped with a mincer plate. The comminuted hydrogel was divided into two halves and dried on wire mesh at different temperatures. The dried hydrogels were coarsely comminuted, ground with a Retsch mill and screened off to a particle size of 150 to 850 μm. The screened-off pulverulent superabsorbent polymers were measured for retention.

In a further run, the pH in the make-up vessel was adjusted to pH 11.3 with 11.5 g of 10% strength aqueous sodium hydroxide solution. The products resulting there from were coated with the crosslinking solution based on citric acid as per Example 2 and post crosslinked at 120° C. for 50 minutes.

TABLE 5

Example 7 Variations

| Precursor No | pH | Drying [° C./h] | TB [g/g] | Post crosslinked product | | |
|---|---|---|---|---|---|---|
| | | | | TB [g/g] | AAP$_{0.3}$ [g/g] | AAP$_{0.7}$ [g/g] |
| 7.1 | 9 | 80/12 | 45.2 | | | |
| 7.2 | 9 | 150/2.25 | 10.6 | | | |
| 7.3 | 11 | 80/12 | 45.2 | 21.0 | 20.5 | 16.1 |
| 7.4 | 11 | 150/2.25 | 55.6 | 28.2 | 20.5 | 16.0 |

This example demonstrates the effect of drying temperature and pH on the internal crosslinking and also the surface of the CMC. Example 7.2 is internally crosslinked at high drying temperatures of 150° C. and has a low retention value. When the drying temperature is lowered (Example 7.1), there is no internal crosslinking.

Internal crosslinking at high temperatures can be prevented by raising the pH, as Example 7.4 shows. The comparison of Example 7.3 with Example 7.4 demonstrates the effect of a high temperature on the properties of the absorbent resins according to the invention. It is believed that drying at high temperatures gives rise to surface hornification, leading to comparable absorbencies against pressure at a significantly higher retention level.

To control internal crosslinking, the pH of the swelling medium for the pretreatment was herein below adapted in such a way (unless otherwise stated) that drying temperatures of 150° C. provided a precursor retention value of at least 40 g/g which did not decrease to below 40 g/g even when the dry precursor was annealed at 120° C. for 60 minutes.

Example 8

Demineralized water is charged to a make-up vessel and mixed with different amounts of 2-propanol. The pH of the solvent is adjusted to a pH 11.7 with 4.7 g of 10% strength NaOH per 1000 ml and carboxymethylcellulose (Cekol® 100,000, degree of neutralization 98.6%) is added with vigorous stirring so that the final concentration of the carboxymethylcellulose based on the entire batch is between 8 and 20% by weight. After a swell time of 1 hour, the swollen hydrogel was fed to a meat mincer equipped with a mincer plate and comminuted. The comminuted hydrogel was dried in a circulating air cabinet at 150° C. for 2.5 hours. The dried hydrogel was coarsely comminuted and ground with a Retsch mill. After the particle size fraction of 150 to 850 μm had been screened off, 50 g of each pulverulent precursor were placed in a plastic dish, stirred using a mixer and sprayed with 4.0 g of a 50% strength aluminum sulphate×14H$_2$O solution in DM water, corresponding to 0.36% of Al$^{3+}$ based on CMC, in the course of 10 seconds. The coated powder was stirred for a further 110 seconds and subsequently dried at 150° C. for 10 minutes. The characteristic absorption data of the dried surface-crosslinked superabsorbent polymers were then determined as shown in Table 6.

TABLE 6

Example 8 Variations

| No | 2-Propanol in solvent [wt %] | CMC in batch [wt %] | TB [g/g] | AAP$_{0.3}$ [g/g] | AAP$_{0.7}$ [g/g] | Bulk density [g/dm$^3$] |
|---|---|---|---|---|---|---|
| 8.1 | 19.8 | 8 | 28.2 | 20.5 | 16.0 | 450 |
| 8.2 | 13.8 | 12 | 23.2 | 17.5 | 13.5 | 490 |
| 8.3 | 7.1 | 16 | 27.3 | 16.7 | 13.2 | 550 |
| 8.4 | 5 | 20 | 28.5 | 16.4 | 13.4 | 570 |
| 8.5 | 3 | 20 | 28.8 | 16.0 | 13.2 | 590 |
| 8.6 | 1 | 20 | 28.8 | 16.0 | 12.8 | 610 |
| 8.7 | 0 | 20 | 27.7 | 14.4 | 12.5 | 650 |

Example 8 shows that as little as less than 5% of isopropanol in the swelling medium will reduce the bulk density of the superabsorbent polymers according to the invention and distinctly improve absorbency against pressure. The results suggest that the rapid vaporization of the solvent in the course of the drying of the precursors results in an increasingly porous particle structure, which is beneficial for the absorbency against pressure in particular.

Example 9

4,800 g of DM water are charged to a make-up vessel and admixed with sodium hydroxide (every 1000 ml of water contain 4.7 g of 10% strength aqueous sodium hydroxide solution) until the pH is 12. 1,200 g of carboxymethylcellulose (Cekol® 100,000, degree of neutralization 98.6%, NaCl content 0.74% by weight) are added with stirring to form a firm hydrogel. After a swell time of 2 hours, the hydrogel was transferred into a mincer equipped with a mincer plate and comminuted. The comminuted hydrogel was dried at 150° C. for 2 hours, coarsely comminuted and ground with a Retsch mill. The particle size fraction of 150 to 850 μm was screened off and the characteristic precursor data were determined:

Example No. 9.1

| TB = 54.8 g/g | AAP$_{0.3}$ = 8.6 g/g | AAP$_{0.7}$ = 8.3 g/g |

50 g of the screened-off precursor product No 9.1 were initially charged, coated with 6 g of a 50% strength solution of Al$_2$(SO$_4$)$_3$×14H$_2$O in DM water (0.54% of Al$^{3+}$ based on CMC) with stirring and dried at 150° C. for 10 minutes:

Example No. 9.2

| TB = 27.7 g/g | AAP$_{0.3}$ = 14.4 g/g | AAP$_{0.7}$ = 12.5 g/g |
|---|---|---|

50 g of the screened-off precursor product No. 9.1 were initially charged, coated with 8 g of a solution of 16.67 g of citric acid monohydrate and 8.33 g of sodium hypophosphite in 25 g of a 37.5% strength solution of polyethylene glycol 1,500 in DM water (5.1% of citric acid, 2.6% of sodium hypophosphite, 3% of PEG based on CMC) with stirring and post crosslinked at 150° C. for 20 minutes.

Example No. 9.3

| TB = 23.0 g/g | AAP$_{0.3}$ = 14.3 g/g | AAP$_{0.7}$ = 11.6 g/g |
|---|---|---|

50 g of the screened-off precursor product No. 9.1 were initially charged, coated with 7 g of a solution composed of 67% by weight of a 50% strength Al$_2$(SO$_4$)$_3$×14H$_2$O solution in DM water and 33% by weight of a 40% citric acid monohydrate solution in DM water (0.43% of Al$^{3+}$ and 1.7% of citric acid based on CMC) with stirring and post crosslinked at 140° C. for 20 minutes:

Example No. 9.4

| TB = 26.3 g/g | AAP$_{0.3}$ = 14.3 g/g | AAP$_{0.7}$ = 12.1 g/g |
|---|---|---|

Example 10

0.5 g of each of the preswollen and crosslinked carboxymethylcellulose No. 9.1 and the differently surface-crosslinked superabsorbent polymers Nos. 9.2 and 9.3 were transferred into 100 ml of 0.9% strength NaCl solution and stirred at room temperature for 16 hours. Extractables were then determined by GPC chromatography. The untreated raw material has a solubility of greater than 80% in this analysis.

|  | Example No | | |
|---|---|---|---|
|  | 9.1 | 9.2 | 9.3 |
| Extractables (%) | 42 | 30 | 21 |

The pretreatment according to the invention is enough to bring about a distinctly reduced solubility for the precursor compared with the raw material used. The subsequent surface crosslinking further reduces the solubility.

Example 11

A: A pulverulent carboxymethylcellulose (Cekol® 100,000, degree of neutralization 98.6%) was coextruded from a twin-screw extruder together with water at different pH values. The total throughput was 56 kg/hour and the carboxymethylcellulose fraction in the hydrogel was 20-25% by weight. The pH of the aqueous solvent was regulated by addition of sodium hydroxide. The extruder screws were equipped with additional kneading elements to improve the homogeneity of the hydrogel. The hydrogel formed was pressed through a breaker plate, the gel extrudates obtained were dried at 150° C. and subsequently ground and screened off to 150-580 μm. The screened pulverulent precursor product was analyzed for its retention:

TABLE 7a

| | Example 11 Variations | |
|---|---|---|
| No | pH of swelling medium | TB [g/g] |
| 11.1 | 7 | 42.9 |
| 11.2 | 8 | 41.8 |
| 11.3 | 9 | 41.0 |
| 11.4 | 10 | 41.1 |

B: A was repeated except that no kneading elements were used at a total throughput of 99 kg of hydrogel per hour. The homogeneity of the gel was visibly inferior to in A. Here and there the gel extrudates contained dry particles.

TABLE 7b

| | Example 11 Variations | |
|---|---|---|
| No | pH of swelling medium | TB [g/g] |
| 11.5 | 7 | 43.1 |
| 11.6 | 8 | 45.2 |
| 11.7 | 9 | 42.7 |
| 11.8 | 10 | 41.6 |

C: B was repeated except that the total throughput was 97-102 kg of hydrogel per hour and the carboxymethylcellulose fraction in the hydrogel was varied between 20 and 45% by weight. The pH of the swelling medium was adjusted to 7.5 with sodium hydroxide in all cases:

TABLE 7c

| | Example 11 Variations | |
|---|---|---|
| No | CMC fraction in hydrogel [wt %] | TB [g/g] |
| 11.9 | 23 | 44.5 |
| 11.10 | 29 | 41.7 |
| 11.11 | 35 | 43.1 |
| 11.12 | 40 | 45.2 |
| 11.13 | 45 | 42.4 |

50 g of each of the pulverulent precursor products of A, B and C were charged to a mixing reactor. The surface of the precursor products was coated with in each case 5 g of a 50% strength aluminum sulphate 14-hydrate solution with stirring. The coated products were each dried at 120° C. for 20 minutes and analyzed for their retention values and their absorbency against pressure:

TABLE 7d

| | Example 11 Variations | | | |
|---|---|---|---|---|
| No | Precursor No | TB [g/g] | AAP$_{0.3}$ [g/g] | AAP$_{0.7}$ [g/g] |
| 11.14 | 11.1 | 25.4 | 16.0 | 12.6 |
| 11.15 | 11.4 | 30.2 | 15.1 | 11.9 |
| 11.16 | 11.5 | 27.0 | 15.9 | 12.7 |
| 11.17 | 11.6 | 31.4 | 15.9 | 12.6 |
| 11.18 | 11.7 | 29.4 | 15.3 | 11.6 |
| 11.19 | 11.11 | 34.4 | 15.9 | 12.9 |

The results show that the superabsorbent polymers according to the invention are obtainable on a large scale by continuous processes, the extrusion operation evidently not being subject to any limitations. Even comparatively less homogeneous gel extrudates, obtained for example by extrusion at high throughput and low water content without the use of kneading elements, do not lead to any impairment in the absorption properties of the absorbent resins according to the invention. Example 11, furthermore, demonstrates the conjoint influence of the pH and of the mixing technology on internal crosslinking. If, as in this case, the mixing operation used continuously supplies the dry raw material with the swelling medium and the swelling medium is not present in excess at any time, precursors which do not internally crosslink in the course of drying are obtained even at pH 7. It is believed that there is a relationship between the degree of solubilization of the raw material and the reactivity with regard to internal crosslinking. The preceding Inventive Examples 1 to 10 had the swelling medium introduced as an initial charge, i.e. the polysaccharides were present in greater dilution at the start of the swelling and were able to assume a more reactive preferred conformation. Raising the pH neutralized the free acid functionalities and hence controlled internal crosslinking.

Example 12

1,200 g of carboxymethylcellulose (Finnfix® 50,000) were preswollen, dried, ground and screened to 150-850 μm, each step being carried out as described in Example 9). 50 g of each screened precursor was coated with a 50% strength solution of $Al_2(SO_4)_3 \times 14H_2O$ in DM water with stirring and dried at 120° C. for 20 minutes. The coated superabsorbent polymers were analyzed for their surface crosslinking index:

TABLE 8

Example 12 Variations

| No | g of 50% $Al_2(SO_4)_3 \times 14H_2O$ sln 50 g of precursor | $C_{SAP}$ $[Al^{3+}]$* | $C_F$ $[Al^{3+}]$* | SCI |
|---|---|---|---|---|
| 12.1 | 4.00 | 0.36 | 0.78 | 42 |
| 12.2 | 5.00 | 0.45 | 0.90 | 45 |
| 12.3 | 7.00 | 0.64 | 1.20 | 56 |

[ ]*in % by weight

Example 13

The absorbency against pressure performance of the pulverulent absorbent resin Example No. 11.17 (Example 11) was tested using the fluff-absorbent combination test against a synthetic superabsorbent (Z1030 product, synthetic pre- and post crosslinked polyacrylic acid polymer having a degree of neutralization=70%, $AAP_{0.3}$=31.6 g/g and $AAP_{0.7}$=24.4 g/g, from Stockhausen GmbH & Co. KG). The following characteristic data were determined from the absorption curve as a function of the concentration of superabsorbent (SAP) as shown in Table 9:

TABLE 9

| | | FACT at 0.3 psi SAP conc. in pad | | | FACT at 0.7 psi SAP conc. in pad | | |
|---|---|---|---|---|---|---|---|
| No. | Parameter | 10% | 31% | 50% | 10% | 31% | 50% |
| 11.17 | $Abs_{max}$ [g/g] | 20.0 | 29.7 | 42.3 | 15.0 | 23.0 | 29.0 |
| | $t_{max}$ [min] | 16 | 27 | 84 | 16 | 25 | 47 |
| | $t_{50\%}$ [min] | 1 | 3 | 9 | 1 | 2 | 7 |
| Z1030 | $Abs_{max}$ [g/g] | 21.8 | 39.7 | 68.5 | 17.4 | 32.8 | 53.5 |
| | $t_{max}$ [min] | 20 | 29 | 48 | 19 | 36 | 69 |
| | $t_{50\%}$ [min] | 2 | 4 | 9 | 2 | 6 | 12 |

Example 13 shows that the absorbency of the absorbent resins according to the invention can be significantly proved by combination with a matrix material relative to a synthetic polyacrylate absorbent. Whereas Example No. 11.17 has less than 50% of the absorbency against a (0.3 and 0.7 psi) pressure value of a Z1030 product, this percentage increases to ≧55% in the case of 50% of SAP in the fluff-SAP mix and up to ≧86% in the case of 10% SAP in the fluff-SAP mix.

Example 14

The crosslinked pulverulent absorbent resin Example No. 11.15 of Example 11 was processed with different cellulose fluff quantities to form an airlaid composite article. A synthetic polyacrylate superabsorbent (Z 1030, Stockhausen) was processed into a composite article under identical conditions for comparison. The composites were characterized for their retention performance and their liquid absorbency against a pressure of 20 or 50 g/cm² as shown in Table 10:

TABLE 10

| | | Airlaid composites | | | | | |
|---|---|---|---|---|---|---|---|
| | | Retention | | LAUL20 (0.3 psi) | | LAUL50 (0.7 psi) | |
| Fluff content in composite | SAP (type) | Absolute [g/m²] | Relative* | Absolute [g/m²] | Relative* | Absolute [g/m²] | Relative* |
| 50% | 11.15 | 6 821 | 86.6 | 7 784 | 65.0 | 6 337 | 67.0 |
| | Z 1030 | 7 878 | — | 11 963 | — | 9 452 | — |
| 70% | 11.15 | 3 566 | 82.1 | 5 284 | 68.9 | 4 314 | 72.2 |
| | Z 1030 | 4 345 | — | 7 673 | — | 5 974 | — |
| 90% | 11.15 | 1 219 | 86.7 | 3 210 | 81.7 | 2 568 | 80.2 |
| | Z 1030 | 1 406 | — | 3 928 | — | 3 199 | — |

TABLE 10-continued

Characteristic data of pure pulverulent superabsorbent resins

| without fluff | SAP (type) | Retention Absolute [g/g] | Relative* | $AAP_{0.3}$ Absolute [g/g] | Relative* | $AAP_{0.7}$ Absolute [g/g] | Relative* |
|---|---|---|---|---|---|---|---|
| — | 11.15 | 30.2 | 97.4 | 15.1 | 47.8 | 11.9 | 48.7 |
| | Z 1030 | 31.0 | — | 31.6 | — | 24.4 | — |

*Z 1030 product = 100

Example 14 shows the performance improvement of superabsorbent polymers according to the invention relative to synthetic supersuperabsorbent polymers in airlaid composites. The more homogeneous mixture of the matrix material with the absorbent is responsible for the fact that this relative performance improvement is even clearer than in Example 13 especially at high absorbent contents in the matrix.

Example 15

Ageing stability was characterized by storing the biodegradable superabsorbent resins for a prolonged period at room temperature and an average humidity of more than 50% and then measuring retention and absorbency against pressure.

TABLE 11

| | Data after synthesis | | | Data after storage | | | |
|---|---|---|---|---|---|---|---|
| Example No | TB [g/g] | $AAP_{0.3}$ [g/g] | $AAP_{0.7}$ [g/g] | Age in days | TB [g/g] | $AAP_{0.3}$ [g/g] | $AAP_{0.7}$ [g/g] |
| 2.3 | 19.4 | 20.9 | 16.8 | 513 | 19.2 | 19.4 | 15.4 |
| 2.4 | 20.4 | 21.8 | 17.2 | 384 | 20.5 | 22.0 | 15.8 |
| 8.1 | 28.2 | 20.5 | 16.0 | 222 | 32.6 | 19.0 | 14.1 |
| 9.2 | 27.7 | 14.4 | 12.5 | 225 | 25.5 | 14.1 | 11.4 |

Example 16

The particle size distribution of the pulverulent superabsorbent polymers was determined before and after ball milling and to characterize the mechanical stability. The data in the table, which follows, are based on the % by weight content of the individual particle size fractions as shown in Table 12:

TABLE 12

| | Particle size fraction before ball milling | | | Particle size fraction after ball milling | | | |
|---|---|---|---|---|---|---|---|
| No | 150-300 μm | 300-600 μm | 600-850 μm | 150-300 μm | 300-600 μm | 600-850 μm | <150 μm |
| 8.1 | 12.8 | 53.6 | 33.6 | 16.0 | 55.6 | 27.4 | 1.0 |
| 11.15 | 19.6 | 53.7 | 26.7 | 21.6 | 51.9 | 25.7 | 0.8 |
| 11.17 | 23.3 | 52.2 | 24.5 | 23.5 | 52.6 | 22.5 | 1.3 |
| 11.19 | 11.0 | 61.6 | 27.4 | 24.6 | 50.7 | 23.4 | 1.3 |

This example demonstrates that the superabsorbent polymers according to the invention are mechanically very robust and will have a similar particle size distribution and only very small <150 μm fines fractions even after a mechanical stress of the kind occurring in product conveying for example. This ensures consistent product properties even after conveying and metering operations.

The examples show that the polymers according to the invention combine very high retention ability with a significantly improved ability to absorb water and aqueous fluids against an external pressure. They further combine good long-term storage stability with good biodegradability under composting conditions. It has also been shown that only the process according to the invention, involving the preparation of a hydrogel followed by drying under conditions leading to hornification but not to internal crosslinking and subsequent surface crosslinking in minimal layer thickness, will provide the unique combination of high retention ability, high absorbency against an external pressure, stability in storage and biodegradability.

What is claimed:

1. A post crosslinked superabsorbent polymer comprising at least one partially neutralized, uncrosslinked, carboxyl-containing polysaccharide that is preswelled and subsequently dried, wherein the dried polycarboxypolysaccharide is surface-post crosslinked by means of a surface crosslinker wherein said post crosslinked superabsorbent polymer has an absorbency against pressure ($AAP_{0.7}$) value of 12.5 g/g or more.

2. The superabsorbent polymer of claim 1 wherein the polycarboxypolysaccharide is derived from starch or cellulose or polygalactomannan or from any combination of at least two thereof.

3. The superabsorbent polymer of claim 1 wherein polycarboxypolysaccharide includes carboxyl groups wherein at least 80% of the carboxyl groups are neutralized.

4. The superabsorbent polymer of claim 1 wherein the carboxyl groups are attached to the polycarboxypolysaccharide at least partially in the form of carboxyalkyl groups.

5. The superabsorbent polymer of claim 1 wherein the polycarboxypolysaccharide has an average degree of carboxyl group substitution of about 0.3 to about 1.5.

6. The superabsorbent polymer of claim 1 wherein the uncrosslinked polycarboxypolysaccharide is characterized by a solution viscosity for a 1% solution of about 2,000 mPas or more.

7. The superabsorbent polymer of claim 1 further comprising carboxyl-free polysaccharides.

8. The superabsorbent polymer of claim 1 wherein the surface crosslinker is present in an amount of about 0.01 to about 25% by weight, based on the polycarboxypolysaccharide.

9. The superabsorbent polymer of claim 1 wherein the surface crosslinker is formed by salts of aluminum cations which are used in an amount of about 0.2 to about 1.0% by weight, based on the polycarboxypolysaccharide.

10. The superabsorbent polymer of claim 1 wherein the surface crosslinker is formed by citric acid used in an amount of about 0.2 to about 8% by weight, based on the polycarboxypolysaccharide.

11. The superabsorbent polymer of claim 1 wherein the surface crosslinker is used in the presence of one or more water-soluble hydrophilic polymers.

12. The superabsorbent polymer of claim 11 wherein the hydrophilic polymers may be polyalkyleneglycols or polyvinyl alcohols.

13. The superabsorbent polymer of claim 1 having a retention of about 15 g/g or more and an absorbency against pressure ($AAP_{0.7}$) value of 13 g/g or more.

14. The superabsorbent polymer of claim 1 having a retention of about 20 g/g or more and an absorbency against pressure ($AAP_{0.7}$) value of 14 g/g or more.

15. The superabsorbent polymer of claim 1 having absorbency against pressure ($AAP_{0.7}$) value for the polymer powder is not less than about 80% of the initial value after ageing for 200 days under standard conditions.

16. The superabsorbent polymer of claim 1 having about 5% or less by weight of fines having a particle size of below about 150 microns after mechanical exposure due to roller milling for 6 minutes.

17. The superabsorbent polymer powder according to claim 1 having a surface crosslinking index (SCD) of about 40 or greater.

18. A post crosslinked superabsorbent polymer comprising at least one partially neutralized, uncrosslinked, carboxyl-containing polysaccharide that is preswelled and dried and surface-post crosslinking the dried polycarboxypolysaccharide by means of a surface crosslinker, wherein the polycarboxypolysaccharide includes one or more water-soluble additives from the group consisting of base, salts and blowing agents or one or more anti-blocking additives from the group consisting of natural fiber materials, synthetic fiber materials, silica gels, synthetic silicas and water-insoluble mineral salts or any combination of at least two there from and wherein said post crosslinked superabsorbent polymer has an absorbency against pressure ($AAP_{0.7}$) value of 12.5 g/g or more.

19. The superabsorbent polymer of claim 18 wherein the surface crosslinker is formed by salts of aluminum cations which are used in an amount of about 0.2 to about 1.0% by weight, based on the polycarboxypolysaccharide.

20. The superabsorbent polymer of claim 18 wherein the blowing agents release a gas under the influence of a catalyst or heat.

21. The superabsorbent polymer of claim 18 wherein the water-soluble additives and antiblocking additives are each included in amounts of about 0.01 to about 20% by weight, based on polycarboxypolysaccharide.

22. The superabsorbent polymer of claim 18 wherein the surface crosslinker is formed by citric acid used in an amount of about 0.2 to about 8% by weight, based on the polycarboxypolysaccharide.

23. A post crosslinked superabsorbent polymer comprising at least one partially neutralized, uncrosslinked, carboxyl-containing polysaccharide that is preswelled and subsequently dried, wherein the polycarboxypolysaccharide is surface crosslinked by means of a surface crosslinker, wherein the surface crosslinker may be ionic or covalent crosslinkers or any combination of these post crosslinking.

24. The superabsorbent polymer of claim 23 wherein the ionic surface crosslinkers are salts of at least divalent cations and the covalent surface crosslinkers are acid-functional substances.

25. The superabsorbent polymer of claim 23 wherein the surface crosslinker is formed by salts of aluminum cations which are used in an amount of about 0.2 to about 1.0% by weight, based on the polycarboxypolysaccharide.

26. The superabsorbent polymer of claim 23 wherein the surface crosslinker is formed by citric acid of about 0.2 to about 8% by weight, based on the polycarboxypolysaccharide.

27. The superabsorbent polymer of claim 23 wherein the covalent surface post crosslinker is used in the presence of one or more crosslinking catalysts.

28. The superabsorbent polymer of claim 23 wherein the ionic surface crosslinkers are salts of at least divalent cations and the covalent surface crosslinkers are acid-functional substances and wherein the covalent surface post crosslinker is used in the presence of one or more crosslinking catalysts.

29. The superabsorbent polymer of claim 23 wherein the covalent surface post crosslinker is used in the presence of one or more crosslinking catalysts selected from the group consisting of mineral acids, Lewis acids, acetylacetonates and hypophosphites.

30. The superabsorbent polymer of claim 23 wherein the ionic surface crosslinkers are salts of at least divalent cations and the covalent surface crosslinkers are acid-functional substances and wherein the covalent surface post crosslinker is used in the presence of one or more crosslinking catalysts selected from the group consisting of mineral acids, Lewis acids, acetylacetonates and hypophosphites.

31. An absorbent post crosslinked polymer comprising at least one partially neutralized, uncrosslinked, carboxyl-containing polysaccharide that is preswelled and subsequently dried and a post crosslinking surface crosslinker, wherein the surface post crosslinking utilizes ionic or covalent crosslinkers or a combination thereof, wherein the ionic surface crosslinkers are salts of at least divalent cations and the covalent surface crosslinkers are acid-functional substances, wherein the polyvalent cation is formed from the group consisting of $Mg^{2+}$, $Ca^{2+}$, $Al^{3+}$, $Ti^{4+}$, $Fe^{3+}$, $Fe^{2+}$, $Zn^{2+}$, and $Zr^{4+}$, and the acid-functional substances are formed from low molecular weight and polymeric polycarboxylic acids and wherein the absorbent post crosslinked polymer has an absorbency against pressure ($AAP_{0.7}$) value of 16 g/g or more.

32. The superabsorbent polymer of claim 31 wherein the surface crosslinker is present in an amount of about 0.01 to about 25% by weight, based on the polycarboxypolysaccharide.

33. The superabsorbent polymer of claim 31 wherein the surface crosslinker is formed by salts of aluminum cations which are used in an amount of about 0.2 to about 1.0% by weight, based on the polycarboxypolysaccharide.

34. The superabsorbent polymer of claim 31 wherein the surface crosslinker is formed by citric acid in the amount of about 0.2 to about 8% by weight, based on the polycarboxypolysaccharide.

35. The superabsorbent polymer of claim 31 wherein the covalent surface post crosslinker is used in the presence of one or more crosslinking catalysts.

36. The superabsorbent polymer of claim 31 wherein the covalent surface post crosslinker is used in the presence of one or more crosslinking catalysts selected from the group consisting of mineral acids, Lewis acids, acetylacetonates and hypophosphites.

37. The superabsorbent polymer of claim 35 wherein the ratio by weight of the surface post crosslinker to the crosslinking catalysts is from about 1:0.001 to about 1:1.

38. An absorbent post crosslinked polymer from a process comprising the steps of a) forming a hydrogel by mixing an uncrosslinked polycarboxypolysaccharide that is preswelled and subsequently dried with water; b) the hydrogel is mechanically comminuted and dried; c) the dried hydrogel is comminuted and classified to form a polymer particles; and d) the polymer particles are coated with a solution of a crosslinker and subjected to a surface post crosslinking and wherein the absorbent post crosslinked polymer has an absorbency against pressure ($AAP_{0.7}$) value of 12.5 g/g/ or more.

39. Absorbent hygiene product comprising an superabsorbent polymer comprising at least one partially neutralized, uncrosslinked, carboxyl-containing polysaccharide that is preswelled and subsequently dried, wherein the dried polycarboxypolysaccharide is surface-post crosslinked by means of a surface crosslinker.

40. The absorbent hygiene product of claim 39 wherein the polycarboxypolysaccharide is derived from starch or cellulose or polygalactomannan or from any combination of at least two thereof.

41. The absorbent hygiene product of claim 39 wherein polycarboxypolysaccharide includes carboxyl groups wherein at least 80% of the carboxyl groups are neutralized.

42. The absorbent hygiene product of claim 39 wherein the carboxyl groups are attached to the polycarboxypolysaccharide at least partially in the form of carboxyalkyl groups.

43. The absorbent hygiene product of claim 39 wherein the polycarboxypolysaccharide has an average degree of carboxyl group substitution of about 0.3 to about 1.5.

44. The absorbent hygiene product of claim 39 wherein the uncrosslinked polycarboxypolysaccharide is characterized by a solution viscosity for a 1% solution of about 2,000 mPas or more.

45. The absorbent hygiene product of claim 39 further comprising carboxyl-free polysaccharides.

46. The absorbent hygiene product of claim 39 wherein the surface crosslinker is present in an amount of about 0.01 to about 25% by weight, based on the polycarboxypolysaccharide.

47. The absorbent hygiene product of claim 39 wherein the surface crosslinker is formed by salts of aluminum cations which are used in an amount of about 0.2 to about 1.0by weight, based on the polycarboxypolysaccharide.

48. The absorbent hygiene product of claim 39 wherein the surface crosslinker is formed by citric acid used in an amount of about 0.2 to about 8% by weight, based on the polycarboxypolysaccharide.

49. The absorbent hygiene product of claim 39 wherein the surface crosslinker is used in the presence of one or more water-soluble hydrophilic polymers.

50. The absorbent hygiene product of claim 39 wherein the superabsorbent polymer has a retention of about 15 g/g or more and an absorbency against pressure ($AAP_{0.7}$) value of 15 g/g or more.

51. The absorbent hygiene product of claim 39 wherein the superabsorbent polymer has absorbency against pressure ($AAP_{0.7}$) value for the polymer powder is not less than about 80% of the initial value after ageing for 200 days under standard conditions.

52. The absorbent hygiene product of claim 39 wherein the superabsorbent polymer has about 5% or less by weight of fines having a particle size of below about 150 .mu.m after mechanical exposure due to roller milling for 6 minutes.

53. The absorbent hygiene product of claim 39 wherein the superabsorbent polymer powder has a surface crosslinking index (SCI) of about 40 or greater.

54. Absorbent hygiene product comprising an superabsorbent polymer comprising at least one partially neutralized, uncrosslinked, carboxyl-containing polysaccharide that is preswelled and dried and surface-post crosslinking the dried polycarboxypolysaccharide by means of a surface crosslinker, wherein the polycarboxypolysaccharide includes one or more water-soluble additives from the group consisting of bases, salts and blowing agents or one or more anti-blocking additives from the group consisting of natural fiber materials, synthetic fiber materials, silica gels, synthetic silicas and water-insoluble mineral salts or any combination of at least two there from and wherein the absorbent post crosslinked polymer has an absorbency against pressure ($AAP_{0.7}$) value of 12.5 g/g or more.

\* \* \* \* \*

UNITED STATES PATENT AND TRADEMARK OFFICE
CERTIFICATE OF CORRECTION

PATENT NO. : 7,407,912 B2 Page 1 of 1
APPLICATION NO. : 10/721821
DATED : August 5, 2008
INVENTOR(S) : Richard Mertens and Olaf Höller It is certified that error appears in the above-identified patent and that said Letters Patent is hereby corrected as shown below:

Column 14,
Line 30, "optionally" should read -- optional --.

Column 23,
Lines 58-59, "Cekol® 100," should read -- Cekol® 100,000, --.

Column 29,
Line 42, "(SCD)" should read -- (SCI) --.

Column 31,
Line 25, "12.5 g/g/" should read -- 12.5 g/g --.

Column 32,
Line 9, "1.0by" should read -- 1.0% by --.

Signed and Sealed this

Third Day of February, 2009

JOHN DOLL
*Acting Director of the United States Patent and Trademark Office*